United States Patent
Bengs et al.

(10) Patent No.: US 6,562,459 B1
(45) Date of Patent: May 13, 2003

(54) METHOD FOR THE PRODUCTION OF SPHERICAL MICROPARTICLES CONSISTING TOTALLY OR PARTLY OF AT LEAST ONE WATER INSOLUBLE POLYGLUCAN CONTAINING BRANCHES AND MICROPARTICLES PRODUCED ACCORDING TO SAID METHOD

(75) Inventors: Holger Bengs, Frankfurt am Main (DE); Jürgen Grande, Bad Soden (DE)

(73) Assignee: Celanese Ventures GmbH, Frankfurt am Main (DE)

( * ) Notice: Subject to any disclaimer, the term of this patent is extended or adjusted under 35 U.S.C. 154(b) by 0 days.

(21) Appl. No.: 09/786,142

(22) PCT Filed: Aug. 14, 1999

(86) PCT No.: PCT/EP99/05976

§ 371 (c)(1),
(2), (4) Date: Jun. 7, 2001

(87) PCT Pub. No.: WO00/12590

PCT Pub. Date: Mar. 9, 2000

(30) Foreign Application Priority Data

Aug. 28, 1998 (DE) .......................................... 198 39 216

(51) Int. Cl.[7] .............................. B32B 5/16; C07H 3/00
(52) U.S. Cl. ...................... 428/402; 536/55.1; 536/112; 536/123.12; 536/124; 536/127
(58) Field of Search .......................... 428/402; 536/55.1, 536/112, 123.12, 124, 127

(56) References Cited

U.S. PATENT DOCUMENTS

| | | | | |
|---|---|---|---|---|
| 4,072,567 A | * | 2/1978 | Yokobayashi et al. | |
| 4,438,200 A | * | 3/1984 | Taubman et al. | |
| 4,766,207 A | * | 8/1988 | Deger et al. | 536/124 |
| 4,908,310 A | * | 3/1990 | Buller | |
| 5,037,972 A | * | 8/1991 | Jamas et al. | 536/114 |
| 5,223,491 A | * | 6/1993 | Donzis | 514/54 |
| 5,281,276 A | * | 1/1994 | Chiu et al. | 127/65 |
| 5,374,442 A | * | 12/1994 | Harris et al. | 426/573 |
| 5,688,775 A | * | 11/1997 | Renn et al. | 514/54 |
| 5,795,979 A | * | 8/1998 | Kusatsu et al. | 536/123.12 |
| 5,827,697 A | * | 10/1998 | Takaha et al. | 435/101 |
| 6,159,257 A | * | 12/2000 | Koutlakis et al. | 51/302 |

* cited by examiner

Primary Examiner—H. Thi Le
(74) Attorney, Agent, or Firm—Marshall, Gerstein & Borun

(57) ABSTRACT

The invention relates to a method for the production of spherical microparticles consisting totally or partly of at least one water-insoluble polysaccharide, wherein the at least one water-insoluble polysaccharide is dissolved in a solvent or solvent mixture, the solution thus formed is introduced into a precipitating agent or precipitating agent mixture, the mixture obtained is optionally cooled and the formed microparticles are separated. The invention is characterized in that the water-insoluble polysaccharide is selected from a polyglucan containing branches with a degree of branching higher than zero and no higher than 8% and a mixture of a polyglucan containing branches and a linear polysaccharide, wherein the proportion of polyglucan containing branches in the mixture is at the most 30% by weight in relation to the overall weight of the polysaccharide and the polyglucan.

32 Claims, 2 Drawing Sheets

3 μm

3 μm

Figure 1:
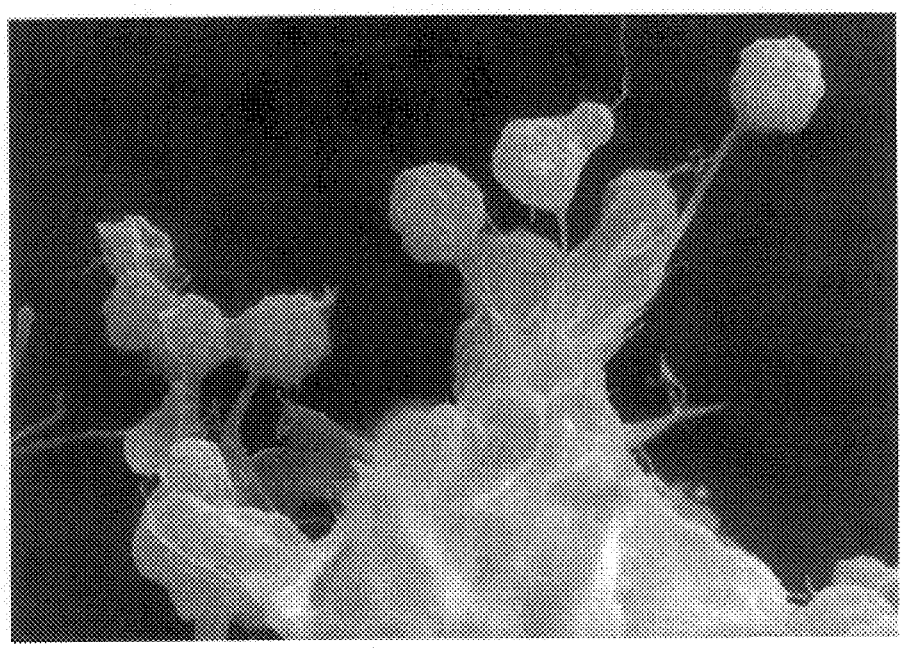

METHOD FOR THE PRODUCTION OF SPHERICAL MICROPARTICLES CONSISTING TOTALLY OR PARTLY OF AT LEAST ONE WATER INSOLUBLE POLYGLUCAN CONTAINING BRANCHES AND MICROPARTICLES PRODUCED ACCORDING TO SAID METHOD

This is the U.S. national phase of International Application No. PCT/EP99/05976 filed Aug. 14, 1999, the entire disclosure of which is incorporated herein by reference.

The present invention relates to a method for preparing spherical microparticles which consist entirely or partly of at least one water-insoluble branchings-containing polyglucan, and also to microparticles obtainable by said method.

The applicant's German patent application No. 19737481.6 which has earlier priority but is not a prior publication describes methods for preparing spherical microparticles containing water-insoluble linear polysaccharides. This method can produce spherical microparticles which stand out in particular due to high uniformity with respect to their shape and their diameter distribution and also due to good mechanical properties.

Owing to their comparatively uniform composition, at the same time, with good mechanical properties, these particles may be employed for a multiplicity of applications.

The starting material used for the method described therein are linear water-insoluble polysaccharides such as, for example, polyglucans which have no branchings or in which conventional methods of measurement cannot detect branchings. Natural linear polysaccharides and polyglucans, however, are not pure. They have therefore either to be isolated or prepared from native sources such as, for example, starch by means of complicated methods or to be obtained via biotechnological methods.

In particular, purifying polysaccharides of natural, for example plant, origin to give compounds with the high linearity required is comparatively time-consuming and costly, so that natural sources have only been of limited use up until now. In view of their general availability and cost-effectiveness, however, extensive usage of the natural sources is desirable.

Surprisingly, it has been found that using polyglucans containing branchings can also produce qualitatively satisfactory spherical microparticles which may be successfully employed for a multiplicity of applications.

Thus, the present invention relates to a method for preparing spherical microparticles which consist entirely or partly of at least one water-insoluble polysaccharide, wherein the at least one water-insoluble polysaccharide is dissolved in a solvent or solvent mixture, the solution formed is introduced into a precipitant or precipitant mixture, the mixture resulting therefrom is cooled, where appropriate, and the microparticles formed are removed, which comprises selecting the water-insoluble polysaccharide from among a branchings-containing polyglucan, which has a degree of branching of greater than zero and not more than 8%, and a mixture of a branchings-containing polyglucan and a linear polysaccharide, in which mixture the proportion of branchings-containing polyglucans is not higher than 30% by weight with respect to the combined weight of the polysaccharide and polyglucan.

The replacement according to the invention of at least part of the linear starting compounds by branchings-containing polyglucans means a substantial simplification and cost reduction of the method described in application No. 19737481.6. The method of the invention simplifies in particular the exploitation of natural polyglucan sources, which makes a cheap and renewable source of raw materials usable for the present invention.

In this respect, the present invention means an advantageous inventive development of the abovementioned German patent application No. 19737481.6.

For the purposes of the present invention, the disclosure of the German patent application No. 19737381.6 is incorporated in its entirety.

The present application further relates to microspherical particles obtainable by the method of the invention.

Figure 2:
Figure 3:
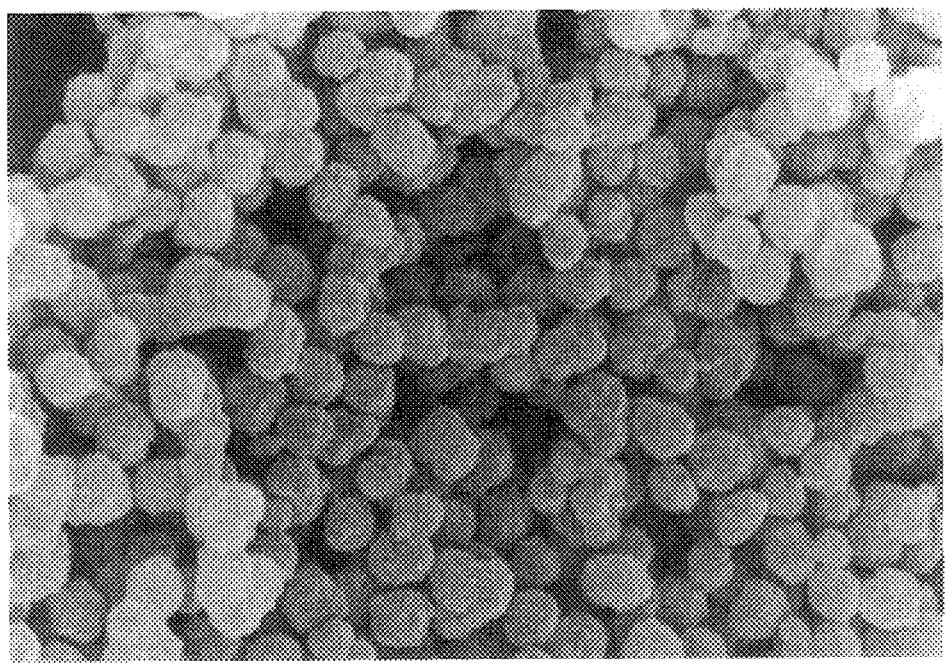
Figure 4:
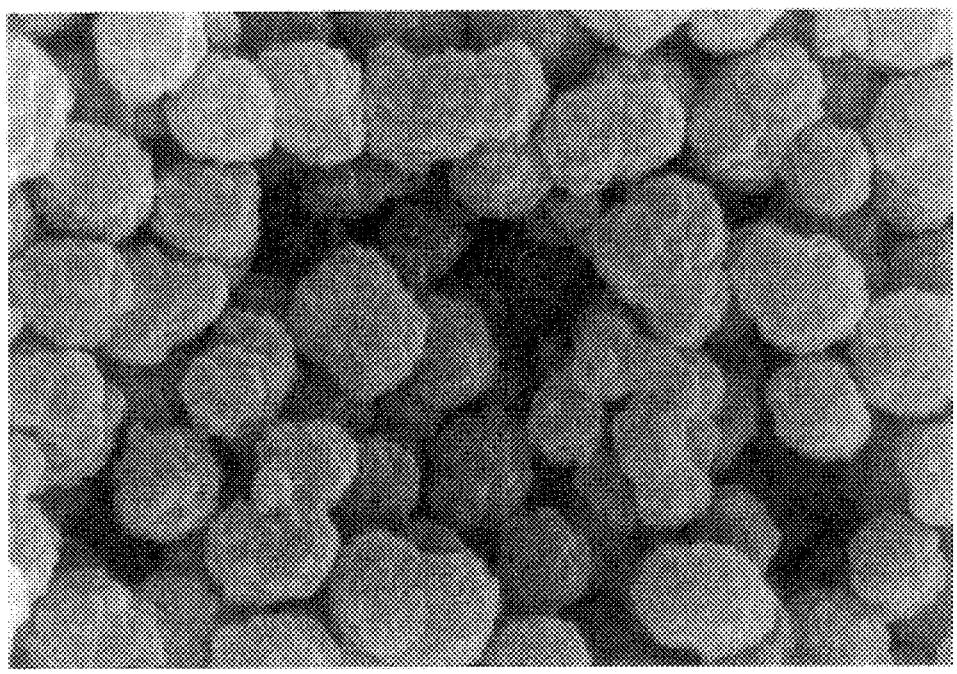

FIGS. 1 to 4 show scanning electron micrographs (SEM, Camscan S-4) of spherical particles according to the invention:

FIG. 1: particles of the invention according to example 1b, magnification 5000×, FIG. 2: particles as in FIG. 1b, magnification 20 000×, FIG. 3: particles of the invention according to example 2, magnification 5000×, FIG. 4: particles of the invention according to FIG. 3, magnification 20 000×.

Polyglucans are composed of glucans as monomeric repeat units which are linked to each other via glycoside bonds. Linearity is present if each monomer in the polymer skeleton is linked via glycosidic bonds to just two further repeat units in the molecule. Exceptions to this are the two repeat units forming the start and the end of the polymer.

If the repeat unit has three or more linkages, then this is referred to as branching. In this context, the number of hydroxyl groups per 100 repeat units, which are not involved in constructing the linear polymer backbone and which form branchings, constitutes the so-called degree of branching DB. Apart from the two hydroxyl groups involved in the formation of the linear polymer backbone, each repeat unit has, in the case of polyglucan, three free hydroxyl groups.

In the present description, the term "polyglucan with branchings" is synonymously used for the expression "branchings-containing polyglucan".

According to a first embodiment, a polyglucan with branchings is employed instead of the linear polysaccharide.

The polyglucan has herein a degree of branching of from greater than 0 to not more than 8%, preferably not more than 5%.

Preferred values for the lower limit of the degree of branching are as follows: greater than 0.5% at position 6 and/or in each case greater than 0.5% and in particular greater than 1% at each of the other positions.

In this first embodiment, it is of course possible to admix any proportions of water-insoluble linear polysaccharide with the polyglucans with branchings.

A higher proportion of linear structure means generally higher uniformity of the microparticles obtained. Particularly uniform particles may be obtained if the proportion of branchings-containing polyglucan is not higher than 30% by weight, preferably not higher than 20% by weight and in particular not higher than 10% by weight.

In a second embodiment, the method of the invention uses a mixture of a water-insoluble linear polysaccharide and a branchings-containing polyglucan, in which the proportion of branchings-containing polyglucan is not higher than 30% by weight, preferably not higher than 20% by weight and in particular not higher than 10% by weight, with respect to the total amount of linear polysaccharide and polyglucan with branchings. In this case, the degree of branching of the polyglucan with branchings is unimportant.

It is true in this case too that the uniformity of the particles generally increases with an increasing proportion of linear structure and a decreasing degree of branching.

The polyglucans used herein may have linkages and branchings at any position of the glucan monomers. Preference is given, however, to polyglucans whose polymer backbone is formed via 1,4-alpha-glycosidic linkages. The branchings may be linked randomly.

According to a preferred embodiment, the polyglucans with branchings used for the invention come from starch or starch analogs which are preferably of plant or animal origin.

A group of starches which may be used within the framework of the invention comprises the starches obtained from plant raw material. These include inter alia starches from tubers such as potatoes, cassavas, arrowroots, yams, from seeds such as wheat, maize, rye, rice, barley, millet, oat, sorghum, from fruits such as chestnuts, acorns, beans, peas and similar pulses, bananas, and also from pith, for example of the sago palm.

The starches obtainable from plant raw material usually and essentially comprise amylose, a poly(1,4-alpha-D-glucan), and amylopectin, a poly(1,4-alpha-D-glucan) with 1,6 branchings, in variable quantitative ratios.

The polyglucans employed according to the invention may also be produced from genetically or biotechnologically modified plants.

The genetic or biotechnological modification may lead, for example, to the production of a polyglucan having a relatively large linear proportion or to a relatively easy separation of the containing starch.

Starch analogs mean compounds which comprise polyglucans but which are not of plant origin. Examples are glycogen, a polyglucan which corresponds to amylopectin and which is of animal origin, and dextran which is obtained from bacteria.

It goes without saying that the branchings-containing polyglucans employed according to the invention may also have been produced biotechnologically, for example using biocatalysis or fermentation.

Modified polyglycans which have been chemically modified, for example by esterification and/or etherification of a hydroxyl group not involved in the formation of the polymer backbone, may also be used. Measures for such modifications are well known to the skilled worker.

So-called alpha-amylase-resistant polyglucans are likewise suitable.

If required, said starch and starch analogs may be purified or treated by any method suited hereto in order to enrich the linear structure.

Suitable purification methods include, for example, separation processes such as absorption methods, precipitation processes with or without further aids, centrifugation, making use of different solubilities, chromatographic methods, etc.

It is also possible to use debranching techniques which chemically or enzymatically decrease branchings in the polyglucan.

For example, enzymes such as amylases, isoamylases, pullulanases or gluconohydrolases cleave branchings off the polymer backbone so that, after their removal, polymers with the desired lower degree of branching are present.

Increasing the linearity is furthermore possible by enzymatically elongating individual chains of branched polyglucans, which reduces the degree of branching.

The linear polysaccharides usable according to the invention may be of any origin. They may have been produced from natural sources which, where appropriate, may have been genetically or biotechnologically modified, or via biotechnological methods. A very advantageous method for the biotechnologial production is described, for example, in WO 95/31 553 which is explicitly referred to here.

They may have been chemically modified, as described above for the branched polyglucans. It is also possible to use alpha-amylase-resistant linear polysaccharides, as [lacuna], for example, in the German patent application No. 198 30 618.0 which has earlier priority but is not a prior publication and which is likewise explicitly referred to here.

It is in particular possible to use the same linear polysaccharides as described in the German application No. 19737481.6.

Preferred examples are linear polyglucans such as poly (1,4-alpha-D-glucan) and poly(1,3-beta-D-glucan), poly(1, 4-alpha-D-glucan) being preferred, in particular when produced biotechnologically.

In the following, the expression "polyglucan/saccharide" is used insofar as the water-insoluble polyglucans with branchings and the water-insoluble linear polysaccharides are referred to together.

For the present invention, the term "water-insoluble polyglucans/saccharides" means compounds which according to the definition of the Deutsches Arzneimittelbuch [German Pharmacopeia] (DAB=Deutsches Arzneimittelbuch, Wissenschaftliche Verlagsgesellschaft mbH, Stuttgart, Govi-Verlag GmbH, Frankfurt, 9th edition, 1987) are classified as "sparingly soluble", "slightly soluble", "very slightly soluble" and "practically insoluble", corresponding to classes 4 to 7.

For the present invention, preference is given to from slightly soluble to practically insoluble compounds, in particular to from very slightly soluble to practically insoluble compounds.

In the case of the polyglucans/saccharides used according to the invention, this means that preferably at least 98% of the amount employed, in particular at least 99.5%, are insoluble in water (corresponding to classes 4 and 5, respectively) under standard conditions (T=25° C.+/−20%, p=101325 Pascal+/−20%).

The following protocol may illustrate "very slightly soluble", corresponding to class 6: One gram of the polyglucan/saccharide to be studied is heated to 130° C. in 1 l of deionized water at a pressure of 1 bar. The solution forming remains stable only briefly for a few minutes. During cooling under standard conditions, the substance precipitates again. After cooling to room temperature and separation by means of centrifugation, at least 66% of the amount employed can be retained, taking into account experimental losses.

The molecular weights $M_w$ (weight average, determined by means of gel permeation chromatography in comparison with a calibration using a pullulan standard) of the polyglucans/saccharides used according to the invention may vary within a wide range from $10^3$ g/mol to $10^7$ g/mol. The molecular weight $M_w$ is preferably in the range from $10^4$ g/mol to $10^5$ g/mol and particularly preferably from $2 \times 10^4$ g/mol to $5 \times 10^4$ g/mol. Another advantageous range is from $2 \times 10^3$ to $8 \times 10^3$.

It has emerged that the molecular weights of the branchings-containing polyglucan may also be higher.

The molecular weight distribution or polydispersity $M_w/M_n$ may likewise vary widely, depending on the origin and preparation method of the polyglucan/saccharide. Preferred ranges are from 1.01 to 50, in particular from 1.5 to 15. Polydispersity increases with a bimodal molecular weight distribution.

As previously mentioned, water-insoluble linear polysaccharides, preferably water-insoluble linear polyglucans, may be admixed according to the invention with polyglucans with branchings.

Other polymers, in particular other biocompatible or biodegradable polymers, may also be added. The amount of the other polymer(s) which is (are) added without changing the spherical shape and/or other properties of the microparticles to be prepared always depends on the polymer added. The amount may be up to 10% or more, with respect to the proportion of polyglucan with branchings and, where appropriate, of linear polysaccharide, and also less in particular cases. The maximum amount allowed depends on the particular individual case and can be readily determined by a skilled worker through standard experiments.

To prepare the microparticles of the invention, the starting materials such as the polyglucan with branchings and, where appropriate, linear polyaccharide, etc. are dissolved in a solvent. Examples of suitable solvents are dimethyl sulfoxide (DMSO), formamide, acetamide, N,N-dimethylformamide, N,N-dimethylacetamide, N-methylmorpholine N-oxide in the presence of water, further N-substituted morpholine N-oxides, aqueous solutions with high or low pH, or mixtures of the abovementioned solvents, DMSO being particularly preferred. It is also possible, of course, to use other solvents familiar to the skilled worker for this purpose.

The total concentration (concentration of polyglucan with branchings plus, where appropriate, concentration of linear polysaccharide) in the solvent may vary within wide limits according to demand. It is preferably in a range from 0.02 g (polyglucan with branchings+polysaccharide)/ml (solvent) to 1.0 g/ml, in particular from 0.05 g/ml to 0.8 g/ml and particularly preferably from 0.3 g/l to 0.6 g/l.

Examples of precipitants are water, dichloromethane, a mixture of water and dichloromethane, mixtures of water and alcohols such as methanol, ethanol, isopropanol, with water and also a mixture of water and dichloromethane being particularly preferred.

The solvent/precipitant ratio is preferably selected within a range from 1:1000 to 1:4 (part of solvent/parts of precipitant) preferably 1:100 to 1:10 and in particular 1:70 to 1:30.

According to a preferred embodiment, the solution containing the starting materials is combined with the precipitant at from 20° C. to 50° C.

If mixing takes place at an elevated temperature, then the mixture being produced may subsequently be cooled, if required.

The order in which solvent and precipitant are combined, for example whether the precipitant is added to the solvent or vice versa, is unimportant in this context. It is, however, important to ensure rapid mixing.

The temperature during the precipitation process is generally maintained at from plus 10° C. to minus 10° C., preferably plus 5° C. and minus 5° C. A higher or lower temperature may be chosen, if required.

The precipitation process may be carried out relatively slowly at low temperature overnight. It can be affected and controlled by varying the temperature and the precipitant.

Furthermore, addition of other precipitation aids may affect the process control and also the properties of the microparticles such as size, etc.

If the mixture of solvent and precipitant is cooled, it must be ensured that said mixture stays liquid and does not solidify.

Examples of suitable precipitation aids are surfactants such as sodium dodecyl sulfate, N-methylgluconamide, polysorbate (e.g. Tween (trademark)), alkyl polyglycol ethers, ethylene oxide/propylene oxide copolymers (e.g. Pluronic (trademark)), alkyl polyglycol ether sulfates, generally alkyl sulfates and glycol fatty acid esters, sugars such as, for example, fructose, sucrose, glucose and water-soluble cellulose derivatives.

The surfactants may be anionic, cationic or nonionic.

It is in principle possible to use any water-soluble cellulose derivative, as long as it is suitable as a precipitation aid. The celluloses in this case may be chemically modified celluloses of any kind. Examples are cellulose esters and cellulose ethers and mixed forms thereof. Specific representatives are, for example hydroxypropylmethylcelluloses, hydroxyethylcelluloses, carboxymethylcelluloses, cellulose acetates, cellulose butyrates, cellulose propionates, cellulose acetobutyrates, cellulose acetopropionates, cellulose nitrates, ethylcelluloses, benzylcelluloses, methylcelluloses, etc.

Mixtures of different water-soluble cellulose derivatives may also be employed.

For the present invention, the term "water-soluble cellulose derivatives" means compounds which according to the definition of the Deutsches Arzneimittelbuch [German Pharmacopeia] (DAB=Deutsches Arzneimittelbuch, Wissenschaftliche Verlagsgesellschaft mbH, Stuttgart, Govi-Verlag GmbH, Frankfurt, 9th edition, 1987) are classified as very soluble to slightly soluble.

Usually, the aids are added to the precipitant. The amount used depends on the particular individual case and also on the desired particle properties, and the skilled worker is familiar with determining the advantageous amount for each case.

Concentrations which have proven to be advantageous are from 2 g (aid)/l (precipitant) to 150 g/l, preferably from 5 g/l to 80 g/l and in particular 8 g/l to 20 g/l. These values in particular also apply to the water-soluble cellulose derivative.

Interestingly, it has emerged that the proportion of particularly small particles can be increased if hot-water-soluble poly-alpha-D-glucan is added to the precipitant.

For this, the same poly-alpha-D-glucan compounds may be employed as those mentioned in connection with the polyglucans with branchings and the linear polysaccharides.

Preferred examples are native or chemically modified starches, poly-alpha-D-glucans obtained from said starches, and also starch-like compounds.

Starch-like compounds mean compounds which comprise poly-alpha-D-glucans but which are not of plant origin. Examples are glycogen and dextran.

The hot-water-soluble poly-alpha-D-glucans may be employed as a mixture of a linear and a branched proportion, as in starch, for example. In this case, the proportion of linear poly-alpha-D-glucan should be greater than 15% by weight, preferably 50 to 99.5% by weight, in particular 60 to 90% by weight and very particularly preferably 65 to 80% by weight, with respect to the total amount of poly-alpha-D-glucan in the precipitant.

They may, however, also comprise branched structures, as in amylopectin or in glycogen, for example.

In the context of the present invention, "hot-water-soluble" means that the poly-alpha-D-glucans are essentially insoluble at room temperature, with the same standard preferably being applied as for the term "water-insoluble" in connection with the branched polyglucans and the linear polysaccharides. The term "solution" or "solubility" means in particular also suspensions or the formation of suspensions like those appearing when dissolving starch.

For example, the hot-water-soluble starches preferred according to the invention have negligible solubility in water at room temperature, while the so-called cold-water-soluble starches are more readily soluble under these conditions.

The hot-water-soluble starches are characterized in particular in that they form solutions when heated under autogenous pressure, for example in an autoclave, to a temperature in the range from about 100 to about 160° C., the particular temperature depending on the type of starch.

It is possible, for example, to dissolve potato starch completely at about 100° C., while maize starch requires approx. 125° C.

For the method of the invention, the hot-water-soluble poly-alpha-D-glucans are preferably added at maximum concentration to the precipitant, i.e. a saturated solution is prepared.

Further suitable ranges are from greater than 0.001% by weight to 10% by weight, preferably from 0.01 to 2% by weight, and in particular from 0.05% by weight to 0.5% by weight, with respect to the amount of precipitant used.

Owing to their natural origin, most of the water-insoluble branchings-containing polyglucans and, where appropriate, water-insoluble linear polysaccharides used according to the invention and degradation products thereof are biocompatible and biodegradable. They are well tolerated in tissues and do not accumulate in the animal, in particular human, body. Biodegradation means in this context any in vivo process leading to degradation or destruction of substances, in this case of the water-insoluble polyglucans/polysaccharides.

These properties of biocompatibility and biodegradability are particularly advantageous for uses concerning human or animal organisms, for example in medicine, pharmacy or cosmetics.

The spherical microparticles which are obtainable according to the method of the invention and which this invention likewise relates to, have a regular spherical shape, narrow size distribution and good mechanical properties, like the microparticles described in the German patent application No. 19737481.6.

The particles may have average diameters (number average) of from 1 nm to 100 µm, preferably 100 nm to 10 µm and particularly preferably 1 µm to 5 µm.

Spherical in accordance with the invention means that the microparticles have nearly a spherical shape. If a sphere is described by axes of identical length which start from a common origin, are directed into space and define the radius of the sphere in all spatial orientations, the length of the axes may deviate from an ideal spherical state by from 1% to 40% for the spherical particles. Preferably, spherical microparticles with deviations of up to 25%, particularly preferably up to 15%, are obtained.

The surface of the spherical microparticles can be macroscopically compared to a raspberry, with the depth of the irregularities on the particle surface, such as recesses or indentations, being not more than 20% of the average diameter of the spherical microparticles.

Furthermore, the microparticles of the invention preferably show a dispersity D=weight average diameter($d_w$)/ number average diameter($d_n$) of from 1.0 to 10.0, preferably from 1.5 to 8.0 and in particular from 2.0 to 4.0.

The averages used herein are defined as follows:

$d_n$=total $n_i \times d_i$/total $n_i$=number average $d_w$=total $n_i \times d_i^2$/total $n_i \times d_i$=weight average $n_i$=number of particles with diameter $d_i$, $d_i$=a particular diameter, i=serial parameter.

The term weight in this connection represents a weighted average. The larger diameters are given greater importance.

It goes without saying that the particles obtainable by the method of the invention are suitable for all applications as listed in the German patent applications Nos. 19737481.6, 19803415.6, 19816070.4 or 19816085.2 which have earlier priority but are not prior publications.

Thus, they can be employed in pure form or as vehicles of active substances in the widest sense, for example

- as additives for cosmetics in ointments, dusting powders, creams, pastes, etc.,
- as vehicles for active substances in pharmaceutical, animal experimental and other similar applications,
- as smoothing agents, for example for closing pores or smoothing flashes,
- as food additive, for example as bulking component or for improving rheological properties,
- as additive for upgrading, for example, emulsion polymers,
- as separation aids, for example in the removal of impurities,
- as encapsulating material,
- as vehicles for magnetic particles, etc.,
- as filler, in particular for biodegradable polymers or industrial polymers, for example for controlling properties,
- as additive for controlling properties, for example the porosity, the weight, the color, etc.,
- as particle standard for calibration or determination of the particle size of unknown materials, etc.,
- as vehicle material for the controlled, e.g. slow, release of active substances
- as bulking agent for improving the properties of industrial or biocompatible polymers, and
- in diagnostic tests, for example as ultrasound agent.

The following examples explain the invention in more detail. These examples serve illustration purposes and are not limiting.

EXAMPLE 1

Preparation of Microparticles Using an Amylose-enriched Starch a. Enrichment of the linear proportion (amylose enrichment):

30 g of starch (Hylon VII, National Starch brand) were stirred in 500 ml of dimethyl sulfoxide (DMSO, Riedel de Haen) at room temperature for 24 hours (h). A cloudy mixture was formed which was centrifuged at 4000 revolutions/minute (rpm) (Labofuge GL from Heraeus) for 20 min. The solution obtained was precipitated in 1:1 butanol, left standing for about 1 h and then filtered. The filter residue was dissolved in 3 l of boiling water. The mixture was cooled to 60° C. and 3 g of thymol (Fluka) were added. The mixture was left standing for 3 days and subsequently boiled for 45 min. After cooling, 1:1 butanol was subsequently added and precipitation took place overnight. The mixture was centrifuged at 4000 rpm for 20 min. The residue obtained was freeze-dried (Freeze-drying apparatus from Christ).

Yield: 11.7 g (39%).

b. Use of amylose-enriched starch for preparing microparticles:

1.0 g of the amylose-enriched starched obtained above was dissolved in 5 ml of DMSO (Riedel de Haen)

within a few minutes at 60° C. The solution was added dropwise and with stirring to 100 ml of water within a few seconds. The mixture obtained was left standing at 5° C. for 16 hours. A fine white precipitate developed in the form of a milky suspension. The precipitate containing the particles was removed by homogeneously suspending the complete mixture and subsequent centrifugation at 3000 rpm for 10 minutes (Labofuge GL from Heraeus). The solid residue obtained was resuspended in double-distilled water three times in total and centrifuged under the same conditions as before. The solid obtained was then resuspended in approx. 10 ml of doubled-distilled water, frozen and lyophilized (Christ Delta 1-24 KD freeze-dryer). To characterize the particles, scanning electron micrographs were produced (SEM, Camscan S-4) which are shown in FIGS. 1 and 2.

On the basis of the images, the particle content was estimated to be about 30%.

c. After repeating the enrichment process described under a., the particle content increased to about 55%, after a third repeat to about 70%.

EXAMPLE 2

Preparation Using a Mixture of Branched and Linear poly(1,4-alpha-D-glucan)

The precipitation process was essentially carried out as described in example 1b. The starting material used was a mixture of 98 mg of poly(1,4-alpha-D-glucan) (98%) and 2 mg of glycogen (2%) from oysters (Fluka).

Yield 65.9 mg (60%).

REM images show a particle content of greater than 95% (FIGS. 4 and 5).

EXAMPLE 3

Preparation Using a Mixture of Branched and Linear poly(1,4-alpha-D-glucan)

The precipitation process was essentially carried out as described in example 1b. The starting material used was a mixture of 90 mg of poly(1,4-alpha-D-glucan) (90%) and 10 mg of amylopectin (10%) (Amioca powder from National Starch).

REM images show a particle content of greater than 85%.

EXAMPLE 4 a. Enzymatic debranching of amylopectin for enrichment of linear structures

A 4-neck stirrer with reflux condenser (polymer apparatus) was charged with 200 ml of deionized water. 50 g of amylopectin (Amioca powder TFL from National Starch) were added. The mixture was heated to 125° C. with stirring and kept at this temperature for 1 h during which the viscosity increased. It was then heated to 130° C. in an autoclave under autogenous pressure for 30 min., and this resulted in a clear, apparently homogeneous viscous solution. The solution was cooled to 58° C. and 60 mg of pullulanase from Bacillus sp. (1.62 U/mg) (Fluka), which had been dissolved beforehand in 1 ml of deionized water, were added. The pullulanase-containing mixture was stirred at 58° C. for 12 h during which the mass became mobile. The solution was then cooled to room temperature and acquired a whitish color in the process. After 6 h hours, a sample (Sample 1) was removed and worked up. The remaining residue was removed after 12 h and freeze-dried (Sample 2).

Yield: 48.5 g b. Use of the enzymatically worked-up amylopectin obtained under a. for preparing microparticles Essentially the same method as in example 1b was applied. The result showed that the proportion of particles formed increases with an increase in linear structures:

Sample 1: about 50% particles
Sample 2: about 80% particles.

EXAMPLE 5

Determination of the Solubility of Polysaccharides and Classification According to the Deutsches Arzneimittelbuch [German Pharmacopeia] (DAB)

564 g of poly(1,4-alpha-D-glucan) in about 0.5 l of double-distilled water were heated in an autoclave (Certoclav apparatus) at 130° C. and 1.3 bar for 1.5 hours. The weight of the autoclave had been determined beforehand. The pressure was then reduced and the apparatus cooled at room temperature. The contents were weighed and corresponded to 501.74 g. After a further 24 hours, the solution was centrifuged and decanted. The solid residue obtained was dried and weighed. From the result of 468 mg, a dissolved proportion of 96 mg is calculated.

With respect to the amount of solvent employed, it follows that 5226 mg of water are required to dissolve 1 mg of poly(1,4-alpha-D-glucan). According to the classification of the DAB, this substance is thus classified as "very slightly soluble". This class includes according to the DAB all substances which require between 1000 and 10 000 parts of solvent in order to dissolve 1 part of the substance.

Of the 7 classes, into which solubility is divided according to the DAB, said class is class 6, with classification ranging from class 1 "very soluble" to class 7 "practically insoluble".

What is claimed is:

1. A method for preparing spherical microparticles comprising at least one water-insoluble polysaccharide, said method comprising the steps of
    (a) dissolving the at least one water-insoluble polysaccharide in a solvent or solvent mixture,
    (b) introducing the solution into a precipitant or precipitant mixture to form a polysaccharide-precipitant mixture, and cooling the polysaccharide precipitant mixture, where appropriate, to form microparticles and,
    (c) removing the microparticles
    wherein said method comprises selecting the water-insoluble polysaccharide from among branched polyglucans having a degree of branching of greater than zero and not more than 8%, and a mixture of branched polyglucans and linear polysaccharides wherein the proportion of branched polyglucans is not higher than 30% by weight with respect to the combined weight of the polysaccharide and polyglucan.

2. The method as claimed in claim 1, wherein the water-insoluble polysaccharide is a mixture of a branched polyglucan which has a degree of branching of greater than zero and not more than 8% and a linear polysaccharide.

3. The method as claimed in claim 1, wherein the branched polyglucan is derived from a plant source.

4. The method as claimed in claim 3, wherein the plant source is starch.

5. The method as claimed in claim 1, wherein the branched polyglucan is derived from an animal source.

6. The method as claimed in claim 5, wherein the animal source is glycogen.

7. The method as claimed in claim 1, wherein the polymer skeleton of the branched polyglucan compromises D-glucan monomers linked via 1,4-alpha-glycosidic linkages.

8. The method as claimed in claim 1, wherein the branched polyglucan has been chemically modified.

9. The method as claimed in claim 1, wherein the branched polyglucan is an alpha-amylase-resistant polyglucan.

10. The method as claimed in claim 1, wherein two or more branched polyglucans are employed.

11. The method as claimed in claim 1, which comprises mixing the solution and the precipitant at from 20 to 50° C. and cooling the resulting mixture to from plus 10° C. to minus 10° C.

12. The method as claimed in claim 11, which comprises cooling the resulting mixture to from plus 5° C. to minus 5° C.

13. The method as claimed in claim 1, wherein the precipitant is water or another aqueous medium.

14. The method as claimed in claim 1, wherein the solvent is dimethyl sulfoxide.

15. The method as claimed in claim 1, wherein the water-insoluble linear polysaccharide is a linear polyglucan.

16. The method as claimed in claim 1, wherein the water-insoluble linear polysaccharide used is poly(1,4-alpha-D-glucan).

17. The method as claimed in claim 1, wherein the water-insoluble linear polysaccharide is poly(1,3-beta-D-glucan).

18. The method as claimed in claim 1, wherein the water-insoluble linear polysaccharide is a chemically modified polysaccharide.

19. The method as claimed in claim 18, wherein the water-insoluble linear polysaccharide has been esterified and/or etherified at at least one of the positions not involved in the formation of the polymer chain.

20. The method as described in claim 19, wherein the water-insoluble linear polysaccharide has been esterified and/or etherified at at least one of positions 2, 3, and 6.

21. A spherical microparticle obtainable according to a method as claimed in claim 1, wherein the surface of the microparticle has recesses or indentations which amount to not more than 20% of the average diameter of the microparticle.

22. The use of spherical microparticles as claimed in claim 21 for separating mixtures of substances.

23. The use of spherical microparticles as claimed in claim 21 as filler in polymers.

24. The use of spherical microparticles as claimed in claim 21 in diagnostic tests.

25. The method as claimed in claim 1, wherein the molecular weight of the polyglucan is in the range of $10^4$ g/mol to $10^5$ g/mol.

26. The method of claim 1 wherein said spherical microparticles consist of said at least one water-insoluble polysaccharide.

27. A spherical microparticle, comprising at least one water-insoluble branched polyglucan having a degree of branching greater then 0 and not more than 8%.

28. The spherical microparticle as claimed in claim 27, which additionally comprises at least one water-insoluble linear polysaccharide.

29. The spherical microparticle as claimed in any of claims 27 or 28, wherein the branched polyglucan is branched poly(1,4-alpha-D-glucan).

30. The spherical microparticle as claimed in claim 27, wherein the water-insoluble linear polysaccharide is linear poly(1,4-alpha-D-glucan).

31. The microparticle as claimed in claim 27, wherein the molecular weight of the polyglucan is in the range of $10^4$ g/mol to $10^5$ g/mol.

32. The spherical microparticles of claim 27 consisting of said at least one water-insoluble branched polyglucan.

* * * * *